US006034133A

United States Patent [19]
Hendley et al.

[11] Patent Number: 6,034,133
[45] Date of Patent: Mar. 7, 2000

[54] USE OF A VIRUCIDAL HAND LOTION TO PREVENT THE SPREAD OF RHINOVIRUS COLDS

[75] Inventors: J. Owen Hendley; Jack M. Gwaltney, Jr.; Deborah F. Thacker, all of Charlottesville, Va.

[73] Assignee: The University of Virginia Patents Foundation, Charlottesville, Va.

[21] Appl. No.: 08/147,742

[22] Filed: Nov. 5, 1993

[51] Int. Cl.$^7$ .............................. A01N 37/00; A01N 31/00
[52] U.S. Cl. ............................................ 514/573; 514/724
[58] Field of Search ..................................... 514/573, 724

[56] References Cited

PUBLICATIONS

Mercki Index 10$^{th}$ Ed 1983 #212.
Andersen 114 CA: 1996627 1991.
Kirschner et al 117 CA 220180h 1992.
Mazer et al 83 CA 1409R 1975.
"Preventing the Spread of the Common Cold", *Research Highlights*, Spring 1990 Gwaltney, Jack M. Jr., Moskalski, Patricia B., and Hendley, J. Owen, "Hand–to–Hand Transmission of Rhinovirus Colds", *Annals of Internal Medicine* vol. 88 No. 4, Apr. 1978, pp. 463–467.
Hendley, J. Owen, Mika, Leonard A., and Gwaltney, Jack M. Jr., "Evaluation of Virucidal Compounds for Inactivation of Rhinovirus on Hands", *Antimicrobial Agents and Chemotherapy*, vol. 14 No. 5, Nov. 1978, pp. 690–694.

Hayden, Gregory F, Deforest, Denise, Hendley, J Owen, and Gwaltney, Jack M Jr., "Inactivation of Rhinovirus on Human Fingers by Virucidal Activity of Glutaric Acid", *Antimicrobial Agents and Chemotherapy*, vol. 26, No. 6, Dec. 1984, pp. 928–929.

Carter, Cathey H, Hendley, J Owen, Mika, Leonard A, and Gwaltney, Jack M Jr., "Rhinovirus Inactivation by Aqueous Iodine in Vitro and on Skin", *Proceedings of the Society for Experimental Biology and Medicine*, vol. 65, 1980, pp. 380–383.

Gwaltney, Jack M. Jr., Moskalski, Patricia B. and Hendley, J. Owen, "Interruption of Experimental Rhinovirus Transmission", *The Journal of Infectious Diseases*, vol. 142, No. 6, Dec. 1980, pp. 811–815.

Gwaltney, Jack M. Jr. and Hendley, J. Owen, "Transmission of Experimental Rhinovirus Infection by Contaminated Surfaces", *American Journal of Epidemiology*, vol. 116, No. 5, 1982, pp. 828–833.

*Primary Examiner*—Russell Travers
*Attorney, Agent, or Firm*—Whitham, Curtis & Whitham

[57] ABSTRACT

Frequent application of a virucidal hand lotion containing malic acid, citric acid, and a $C_{1-6}$ alcohol will prevent the hand-to-hand transmission of rhinoviruses and reduce the incidence of the "common cold" caused by rhinoviruses.

6 Claims, No Drawings

USE OF A VIRUCIDAL HAND LOTION TO PREVENT THE SPREAD OF RHINOVIRUS COLDS

BACKGROUND OF THE INVENTION

1. Field of the Invention

The invention is generally related to preventing the spread of the common cold and protecting individuals from becoming infected with viruses which cause the common cold. More particularly, the invention is related to the use of a composition which effectively kills rhinoviruses present on a person's hands and continues to kill rhinoviruses for a period of hours after application of the composition.

2. Description of the Prior Art

Rhinoviruses are the most significant microorganisms in causing the acute respiratory illness referred to both physicians and lay persons as the "common cold". Other viruses, such as parainfluenza viruses, respiratory syncytial viruses, enteroviruses, and coronaviruses, are known to cause symptoms of the "common cold"; however, rhinoviruses are now thought to cause the greatest amount of cases of the common cold. Rhinoviruses have also been found to be among the most difficult to kill of the cold causing viruses. While the molecular biology of rhinoviruses is now understood in great detail, the progress in determining effective methods for preventing colds caused by rhinoviruses and for preventing the spread of the virus to non-infected subjects has been slow.

Gwaltney et al., *Annals of Internal Medicine*, 88:463–467 (1978) reports that rhinovirus colds are commonly spread amongst a human population by hand-to-hand transmission. That is, one subject with a rhinovirus cold will have a brief physical contact with another subject. By virtue of the physical contact, rhinovirus particles will be present on the hands of the contacted person. The contacted person will then become infected with the rhinovirus by placing contaminated fingers on their nasal and conjunctival mucosa. This hand contact/self inoculation concept for rhinovirus transmission is supported by other research groups that have demonstrated that rhinovirus is recoverable from the hands of a large number of patients infected with rhinovirus.

Hendley et al., *Antimicrobial Agents and Chemotherapy*, 14:690–694 (1978) explored the idea of interrupting the spread of rhinoviruses through the use of antimicrobial liquids and foams applied to the hands. While it is acknowledged that frequent hand washing with ordinary soap and water will mechanically remove viruses from the hands and, thus, reduce the spread of rhinovirus colds, washing one's hands multiple times is irritating to the skin. Therefore, an objective of Hendley et al. was to evaluate the virucidal activity of certain agents that were believed to be non-irritating to the skin after multiple applications so that the need for mechanical removal of the virus by frequent washing was avoided. In Hendley et al., liquids containing dilute iodine in ethyl alcohol or water, and foams containing ethyl alcohol, benzalkonium chloride (BAK), and hexachlorophene were evaluated. The most effective treatment antiviral compositions contained iodine. In addition to immediately killing rhinoviruses on contact, iodine solutions were found to have a residual killing capacity that would inactivate rhinoviruses introduced on a subject's fingers for up to one hour after iodine application. By contrast, ethyl alcohol alone was not effective, and the combination of ethyl alcohol with BAK was fairly ineffective in killing rhinoviruses.

Despite the teachings in Hendley et al., iodine based washes are unsuitable for wide spread use in preventing the spread of rhinovirus induced colds. This is because iodine will cause some brown staining of a patient's hands and is somewhat irritating to the skin.

Hayden et al., *Antimicrobial Agents and Chemotherapy*, 26:928–929 (1984) also discussed the concept of interrupting the hand-to-hand transmission of rhinovirus colds through the use of a safe, cosmetically acceptable hand lotion which has lasting virucidal activity. In Hayden et al., it was discovered that hand lotions containing 2% glutaric acid were more effective than placebo in inactivating certain types of rhinovirus. However, Hayden et al. reports that the glutaric acid containing lotions were not effective against a full spectrum of rhinovirus serotypes.

The Kimberly-Clark Co. has produced a "virucidal tissue" designed for use by persons infected with the common cold. The virucidal tissue includes citric acid, malic acid and sodium lauryl sulfate. Hayden et al., *Journal of Infectious Diseases* 152:493–407 (1985) reported that use of paper tissues, whether treated with virus-killing substances (Kimberly Clark) or untreated, can interrupt the hand-to-hand transmission of viruses. Hence, no distinct advantage in preventing the spread of rhinovirus colds can be attributed to the use of virucidal tissues.

Furthermore, virucidal tissues would have to be used appropriately by infected individuals in order to be effective, not "well" individuals who are not currently suffering from the common cold. In many settings, e.g., the family home, elementary school, in college dormitories, etc., people are in close contact for extended periods of time. As discussed above, this close contact is liable to result in an infected individual transmitting the virus to an unprotected individual. It would be advantageous to have a treatment regime which can be used by both infected and non-infected individuals to halt the spread of the rhinovirus induced colds.

SUMMARY OF THE INVENTION

It is an object of this invention to provide a method for preventing the spread of rhinovirus induced colds.

It is another object of this invention to provide a rhinovirus cold controlling process which employs a virucidal hand lotion that will effectively kill viruses and halt the hand-to-hand transmission of the virus.

According to the invention, a virucidal hand lotion having ethyl alcohol, citric acid, and malic acid in combination has a synergistic rhinovirus killing capacity. The lotion will be applied to the hands of infected individuals to kill rhinoviruses and prevent those individuals from transmitting the disease. In addition, non-infected or "well" individuals will periodically apply the lotion to their hands to reduce the likelihood of acquiring a rhinovirus infection. The lotion has the advantage of being both cosmetically appealing and non-irritating to the skin.

DETAILED DESCRIPTION OF THE PREFERRED EMBODIMENTS OF THE INVENTION

Ethyl alcohol, citric acid, and malic acid have been discovered to act together synergistically in eradicating rhinovirus on the hands of human subjects. A series of experiments were conducted using test hand lotions which demonstrate the synergy. In the experiments, participants followed the following testing procedure:

First, the subjects washed their hands with bar soap and then dried their hands with paper towels. Second, two milliliters (2 ml.) of a test hand lotion was applied to the hands of the participants, the excess was shaken off, and then an additional 2 ml. of the test hand lotion was applied with the excess being shaken off. Third, the test solution was allowed to dry on the hands of the participants. Drying times ranged between three and sixty minutes. Fourth, a drop of viral suspension was applied to the four finger pads of each hand. The viral suspension had a rhinovirus titer of approximately $10^{3.5}$ Tissue Culture Infective Dose (50)/ml (TCID$_{50}$/ml). At least six different serotypes of rhinovirus were examined including serotypes 2, 10, 14, 16, 29, and 39. Application of the viral suspension was achieved by touching the finger tip to a dispensed droplet. Fifth, the viral suspension was allowed to dry on the finger tips for ten to fifteen minutes. Sixth, after the viral suspension had been dried to the finger pads, the four finger pads of each hand were rinsed with 1 ml. of collecting broth. The rinse collections for the right and left hands of each subject were stored separately. Seventh, a viral titration of the collection broth was performed for each rinse collection to determine the amount of viable virus remaining on the finger tips. Standard tissue culture methods were used to determine the amount of viable virus (see procedures described in *Diagnostic Procedure for Rickettsial and Chlamydial Infections*, 5th ed., Ed. E. H. Lennette and N. J. Schmidt, Publisher-American Public Health Association, Washington, D.C. (1979)).

Iodine was used as a positive control for viral eradication and water was used as a negative control. In the experiments, the iodine or water control was applied instead of a test hand lotion. Eradication of virus was defined as detecting less than $10^0$ TCID$_{50}$ per ml of collecting broth ($<10^0$/ml). Eradication of the virus is preferred for a virucidal hand lotion because only one viral particle reaching the eyes or nose will be sufficient to cause infection.

Table 1 presents the viral titers detected for iodine and water control treated hands, for hands treated with a hand lotion containing only citric and malic acid or hands treated with a hand lotion containing only ethanol, and for hands treated with a hand lotion containing citric acid, malic acid, and ethanol.

TABLE 1

| Hands Treatment | TCID$_{50}$/ml | No. of replicates |
|---|---|---|
| Water (negative control) | $10^2$–$10^{3.5}$ | 25 |
| Iodine (positive control) | $<10^0$ | 12 of 20 |
| Citric and Malic acid | $<10^0$ | 3 of 34 |
| (reduced only) | $<10^2$ | 24 of 34 |
| Ethanol | $<10^0$ | 0 of 2 |
| Citric Acid, Malic Acid and Ethanol | $<10^0$ | 32 of 32 |

Table 1 demonstrates that the combination of ethanol, citric acid, and malic acid is as effective as iodine in eradicating the rhinovirus. By contrast, hand lotion with only citric acid and malic acid merely reduced the incidence of viable rhinoviruses on the hands of an individual, it did not eradicate the rhinovirus. Since only a single rhinovirus particle is required for infection of an individual, reducing the numbers of rhinoviruses but not eradicating the rhinoviruses altogether is not acceptable for an application where the desire is to halt the hand-to-hand transmission of the virus. The test solution that contained only ethanol did not eradicate the rhinovirus and this confirms the earlier results of Hendley et al. discussed supra.

Rhinoviruses are known to be hardy viruses and have the ability to survive on a table top or other dry surface for more than four days. Most viruses are killed upon exposure to a 70% ethanol solution; however, rhinoviruses remain viable upon exposure to ethanol. Since rhinoviruses are the major known cause of the "common cold", an antiviral hand lotion needs to be active against the rhinovirus. As is evidenced by Table 1, the combination of malic acid, citric acid and ethanol is required for eradication of rhinoviruses.

In addition to destroying rhinoviruses immediately, it has also been observed that the combination of citric acid, malic acid, and ethanol has a prolonged killing activity. Experiments have shown that rhinovirus suspensions applied to hands previously treated with a virucidal hand lotion containing citric acid, malic acid, and ethanol, up to two hours prior to application of the rhinovirus suspension, are immediately destroyed by the latent activity of the hand lotion. It is expected that the hand lotions can have even longer durations of killing activity (e.g., eight to twelve hours would be ideal).

In operation, a person suffering from a rhinovirus cold or a person who is likely to be exposed to other individuals suffering from rhinovirus colds will periodically apply a virucidal hand lotion that contains the malic acid, citric acid, and alcohol ingredients to his or her hands. This application will kill rhinovirus particles present on the hands of infected individuals, and will kill rhinovirus particles that are transmitted to non-infected individuals via hand-to-hand transmission that are protected by the hand lotion treatment. This treatment procedure will avoid the skin irritation which results from frequent hand washing as a protective measure, and will avoid the cosmetically unfavorable brown color associated with iodine based solutions.

The test solutions used in the experiments described supra included the following in volumetric proportions (w/v): 2% malic acid, 2% citric acid, 70% ethyl alcohol, 1–3% skin lubricant (glycerin, etc.), and the balance water and sufficient base to adjust the pH to about 4.0 (slightly more acidic than tap water). However, it should be understood that the percentages of the constituents can vary within the scope of this invention. For example, including up to 5% each of the malic and citric acids in the hand lotion should not result in skin irritation problems, and the rhinovirus killing synergy of the ethyl alcohol, malic acid, and citric acid combination should be retained if the percentage concentration of the ethyl alcohol ranges from 25–90%. Other short chain alcohols (1–6 carbons ($C_{1-6}$)) such as isopropyl alcohol have also been found to be effective substitutes for ethyl alcohol in terms of producing a synergistic rhinovirus killing activity when combined with malic acid and citric acid; hence, variation in the choice of alcohol is deemed to be within the scope of this invention. With particular regard to the skin lubricant, it is expected that commercially available hand lotions might serve as a suitable base for the hand lotion, and that the skin lubricant could include perfumes, dyes, and other constituents. The skin lubricant could probably range up to 40% w/v of the hand lotion; however, it would be advantageous if the hand lotion did not have a "greasy" feel, since the proper use of this product will require users to get in the habit of periodically applying the hand lotion to their hands. The pH of the hand lotion should also be adjusted to a level that is not irritating to the skin. The preferred pH of the hand lotion would be between pH 3 and pH 6. While the invention has been described in terms of a person spreading a virucidal hand lotion over his or her hands, it is anticipated that the constituents might also be sprayed on the hands, or be applied by other means.

While the invention has been described in terms of its preferred embodiments, those skilled in the art will recognize that the invention can be practiced with modification within the spirit and scope of the appended claims.

We claim:

1. A method for killing rhinoviruses and preventing the spread of rhinovirus induced colds, comnprising the steps of:
   identifying a patient who is suffering from a rhinovirus cold or is likely to be exposed to rhinoviruses; and
   applying to the hands of said patient a virucidal composition comprising citric acid, malic acid, and $C_{1-6}$ alcohol, said virucidal composition including said citric acid, malic acid, and $C_{1-6}$ alcohol in amounts suitable for eradicating rhinoviruses, said step of applying being performed after said patient is identified as suffering from a rhinovirus cold or prior to said patient being exposed to rhinoviruses.

2. The method of claim 1 wherein said step of applying is performed by dispensing said virucidal composition onto the hands of said patient in the form of a lotion which can be spread on the hands by said patinent.

3. The method of claim 1 wherein said step of applying is perform ed multiple times within a twenty four hour period.

4. A method for protecting against infection by rhinoviruses, comprising the step of applying to the hands of a patient in need of protection from rhinovirus infection a virucidal composition comprising citric acid, malic acid, and a $C_{1-6}$ alcohol, said virucidal composition including said citric acid, malic acid, and $C_{1-6}$ alcohol in amounts suitable for eradicating rhinoviruses.

5. The method of claim 4 wherein said step of applying is performed prior to said patient being exposed to rhinoviruses.

6. The method of claim 4 wherein said step of applying is performed multiple times within a twenty four hour period.

* * * * *